| [19] | | [11] | 4,250,872 |
|---|---|---|---|
| | | [45] | Feb. 17, 1981 |

[54] BLOOD PULSATING AND/OR PUMPING DEVICE

[76] Inventor: Yehuda Tamari, 515 Queen St., Westbury, N.Y. 11590

[21] Appl. No.: 909,567

[22] Filed: May 25, 1978

Related U.S. Application Data

[63] Continuation-in-part of Ser. No. 761,169, Jan. 21, 1977, abandoned.

[51] Int. Cl.³ .............................................. A61B 1/03
[52] U.S. Cl. ................................. 128/1 D; 417/394; 417/385
[58] Field of Search ............... 128/1 D, 214 R, 214 F, 128/DIG. 3; 3/1.7; 417/384, 385, 388, 394, 474, 478–480

[56] References Cited

U.S. PATENT DOCUMENTS

| 761,162 | 5/1904 | Gold | 137/517 |
|---|---|---|---|
| 3,406,633 | 10/1968 | Schomburg | 417/474 |
| 3,478,695 | 11/1969 | Goranson et al. | 417/394 |
| 3,630,644 | 12/1971 | Bellhouse | 417/394 X |
| 3,639,084 | 2/1972 | Goldhaber | 417/394 |
| 3,814,547 | 6/1974 | Kitrilakis et al. | 417/383 |
| 3,955,557 | 5/1976 | Takagi | 128/1 D |
| 4,080,958 | 3/1978 | Bregman et al. | 128/1 D |
| 4,116,589 | 9/1978 | Rishton | 417/384 |

OTHER PUBLICATIONS

Wakabayashi et al., *Archives of Surgery*, vol. 105, Jul. 1972, pp. 36–41.

Klain et al., *Trans. Amer. Soc. Artif. Inter. Orgs.*, vol. XVI, 1970, pp. 400–408.

Eguchi et al., *Surgery*, vol. 63, No. 3, Mar. 1968, pp. 490–495.

Wildevaur et al., *Trans. Amer. Soc. Art. Inter. Orgs.*, vol. XIV, 1968, pp. 276–283.

*Primary Examiner*—Dalton L. Truluck
*Attorney, Agent, or Firm*—Watson, Leavenworth, Kelton & Taggart

[57] ABSTRACT

A continuous length of flexible polymeric tubing having a smooth fissureless inner surface throughout is provided with a region intermediate its ends which region has an inside diameter greater than the inside diameter of the remainder of said tubing and a thinner wall than that of the remainder of said tubing with a gradual transition in wall thickness and diameter therebetween. A rigid walled enclosure surrounds said region of the tubing with a slight clearance therebetween except at the ends of the enclosure which encircle the tubing beyond said region with a snug fit. A duct is joined to the enclosure near one end for feeding fluid under pressure thereto. Various arrangements of over-pressure relief prevent pinching of the tubing while affording controlled indentation thereof. The transition section of the tubing wall can cooperate with a port in the enclosure to afford said overpressure relief. Portions of the tubing wall may be thickened (i.e., strengthened) or attached to the enclosure to limit indentation.

19 Claims, 20 Drawing Figures

BLOOD PULSATING AND/OR PUMPING DEVICE

This application is a continuation-in-part of application Ser. No. 761,169, filed Jan. 21, 1977, for "PULSATOR", now abandoned.

The present invention relates to a blood pulsating and/or pumping device for use in procedures involving transporting blood between two cannulae inserted in the body of a patient.

Many procedures are currently employed wherein the heart is externally bypassed either entirely or in part with or without a bypass of the lungs. In a typical procedure, venous blood is removed from the venae cavae and transported through extracorporeal equipment including a pump, generally an oxygenator, although not necessarily, and occasionally a pulsator. Additionally, there may be included filters and other auxiliary equipment.

The best known pump employed for the above purpose is the roller pump which is normally characterized by the ability to provide a continuous or constant flow. There has appeared in the literature description of a roller pump capable of pulsatile flow but such is the exception rather than the general rule. Since pulsatile flow can be superior to non-pulsatile flow insofar as its effect upon the human body, it is desirable to provide for the convenient interposition of a pulsator to superimpose pulsatile flow upon the normal constant flow of the roller pump.

In a typical system, cannulae are inserted into the venae cavae for collection of blood therefrom and connected through tubing to an oxygenator wherein oxygen is added to the blood and carbon dioxide removed therefrom. An additional length of tubing is used to conduct oxygenated blood from the oxygenator through the roller pump and, in the absence of a pulsator, directly to the arterial cannulae. When a pulsator is included the tube from the roller pump is attached by a connector to a pulsator inlet while the pulsator outlet is connected by a separate connector to a further length of tubing leading to the arterial cannulae.

A pulsator is basically a blood reservoir disposed within a rigid housing and provided with an inlet and an outlet that extends beyond the housing for suitable coupling to interconnecting lengths of tubing. A construction known prior to the present invention includes a rigid housing and a cylindrical polyurethane balloon disposed therein. The balloon narrows down at both ends into opposite necks which are carried through the housing and secured thereto. When the pulsator is installed in a circuit, separate lengths of tubing, usually of polyvinyl chloride, are coupled to the respective necks of said balloon by various coupling means including metal bands and possibly overlying shrink tubing and cement. In use, blood flows through the balloon or reservoir and a pulse is superimposed on the steady roller pump flow by alternately increasing and decreasing the pressure in the space between the housing and the reservoir balloon, generally by the introduction thereto or withdrawal therefrom of pressurized air. Such a pulsator suffers from various drawbacks, primarily with respect to the blood "seeing" material and/or surface discontinuities at the pulsator couplings which tend to reduce blood compatibility. A further drawback is implicit in the requirement for separately coupling interconnecting tubing to the pulsator with the necessary clamps and the like. This adds to inconvenience in manufacture and to leaks at the joints.

A further drawback found with the known pulsator is that the balloon outlet is thin walled and tends to collapse or fluctuate under certain conditions. Such collapse tends to occur as a consequence of liquid flow through the narrowing outlet orifice, giving rise to a regional decrease in internal pressure which favors the preferential collapse of the walls of the balloon at such outlet. Once the balloon commences to collapse at the outlet, it will cause an increase in blood velocity, a decrease in internal pressure and further collapse leading to fluttering. Such collapse and flutter at the outlet before the end of the ejection cycle obstructs the pulsator outflow creating extreme negative and positive pressure fluctuations at such outlet that can damage blood and form microbubbles in the blood.

Any device which is used to handle blood must, in addition to the obvious requirement of compatibility, be characterized such that there is an avoidance of excess working of such blood which might cause damage thereto. For example, in a pulsator, if the walls of the pulsator are permitted to collapse or indent to the point of touching they are likely to abrade and damage the blood cells. It is also important to provide directional control over the flow through the pulsator and to avoid any velocity sensitive constriction as noted above. A pulsator should not allow the blood it ejects to come to an abrupt halt either due to the outlet constricting or due to the pulsator becoming empty during ejection. A sudden interruption of moving liquid can cause extreme negative pressures that can cause damage to the blood and formation of microbubbles. A satisfactory pulsator must have a fast response in order that the selected input control is reflected in the output effect upon the blood flow. Another problem with conventional pulsators is the possibility of trapping driving fluid between the balloon or reservoir and the housing preventing complete filling and causing an uneven operation. For best blood compatibility any blood circuit should have no material or physical discontinuities. Prior to this invention, where joints were encountered between components, the inner surfaces were coated with a solution of polyurethane in order to present a smooth environment to the contained blood.

With the foregoing in mind, it is an object of the present invention to provide a novel blood pulsating and/or pumping device for use in procedures involving transporting blood between two cannulae inserted in the body of a patient. It is a further object to provide a system for bypass procedures wherein pulsatile flow and/or counterpulsation to a patient is provided for pumped blood by means of a unitary tubing and pulsator device.

A further object of the present invention is to provide such a device with means for preventing back flow from the pulsator.

A still further object of the present invention is to provide a system and device for pulsatile flow, counterpulsation and/or pumping which is convenient to assemble, efficient in its use, reliable, and gives rise to minimum damage to pumped blood as well as minimizing the possibility of forming microbubbles in said blood.

In accordance with one aspect of the present invention, there is provided a blood pulsating and/or pumping device for use in procedures involving transporting blood between two cannulae inserted in the body which comprises a continuous length of blood compatible flexible polymeric tubing having a smooth fissureless inner surface throughout and a region intermediate the ends of said tubing which region has an inside diameter greater than the inside diameter of the remainder of said tubing and a thinner wall than that of the remainder of said tubing with a gradual transition in wall thickness and diameter therebetween, a rigid walled enclosure surrounding said region of said tubing with a slight clearance therebetween except at the ends of said enclosure which encircle said tubing beyond said region with a snug fit, and a duct joined to said enclosure near one end for interconnecting the space between said enclosure and said tubing region at said one end with a driving unit for controlling the supply thereto and withdrawal therefrom of pressurizing fluid.

Other objects, features and advantages of the present invention will become more apparent by reference to the following detailed description of the presently preferred, but nonetheless illustrative, embodiments thereof with reference to the accompanying drawings wherein:

Reference should now be had to the drawings wherein the same reference numerals are used throughout to designate the same or similar parts.

Figure 1:
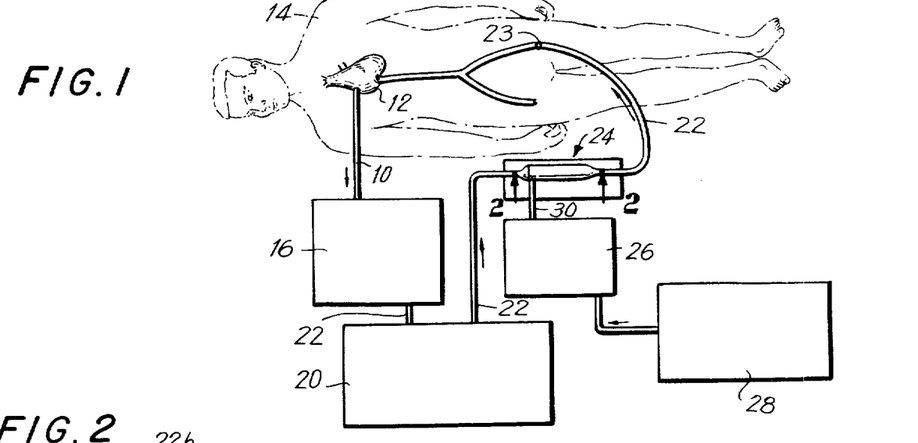
FIG. 1 is a schematic representation of a system according to the present invention and showing particularly a pulsator and unitary tubing with an associated driving unit for controlling the supply thereto and withdrawal therefrom of pressurizing fluid.

A typical system to which the device in accordance with the present invention may be applied is shown in FIG. 1 as including a section of tubing 10 inserted at one end by means of cannulae (not shown) in the venae cavae for obtaining venous flow from the heart 12 of the patient 14. Tubing 10 is coupled, as an example, to oxygenator 16 wherein oxygen is supplied to the blood and carbon dioxide removed. Blood from oxygenator 16 is then conducted by means of unitary tubing 22 through a roller pump 20 whose function it is to pump the blood through the unitary tubing 22 to the arterial cannula (not shown) located in the femoral artery at 23. Thus, unitary tubing member 22 passes through pulsator 24 from roller pump 20 to the patient 14. A driving unit 26 is used in conjunction with a source of fluid under pressure 28 to provide through conduit means 30 a controlled flow and withdrawal of pressurized fluid to and from pulsator 24.

Figure 3:
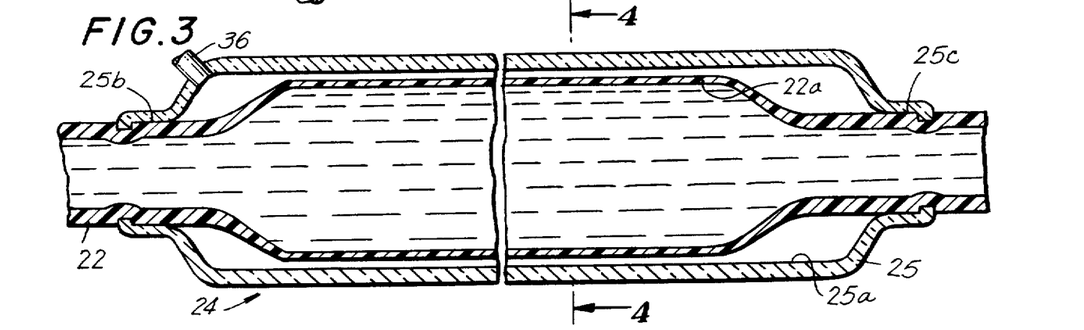
FIG. 3 is a sectional view of one preferred embodiment of a pulsator, wherein a unitary tubing member is sealed within a rigid housing for operation according to the present invention.

Referring to FIG. 3, one presently preferred embodiment of the pulsator 24 is shown to include a unitary tubing member 22 passing through a generally cylindrical housing or enclosure 25 which is of rigid construction using a material such as Lexan or the like. Tubing member 22 should consist of a continuous length of blood compatible flexible polymeric material having a smooth fissureless inner surface throughout. For example, it may be formed from polyvinyl chloride or the like. As shown, it has a region 22a intermediate its ends which region has an inside diameter greater than the inside diameter of the remainder of said tubing and a thinner wall than that of the remainder of said tubing with a gradual transition in wall thickness and diameter therebetween. The rigid walled enclosure 25 surrounds said region 22a of said tubing with a slight clearance therebetween throughout the housing cavity 25a. Inlet opening 25b and outlet opening 25c of housing 25 are sealed to the smaller diameter normal section of tubing member 22 on either side beyond the central region 22a. A duct 36 is joined to the housing 25 near one end for interconnecting the space between the housing 25 and the tubing region 22a at said one end with the driving unit 26.

During operation of the device, pressurized fluid is introduced through duct 36 into the housing cavity 25a when it is desired to pulse the blood whereupon it causes indentation or contraction of the thin walled section or region 22a of the tubing to displace any blood contained therein. By appropriately tailoring the wall thickness of the plastic tubing in the region 22a relative to the normal wall thickness of the tubing beyond the expanded section, or by tailoring the snugness of the fit between tubing 22 and inlet opening 25b and/or outlet opening 25c, it is possible to arrange for the tubing where it passes through the ends of the housing to indent slightly in response to excess fluid pressure within cavity 25a creating a vent passage and precluding pressure build-up beyond a predetermined level. Thus, a safety feature is built into the design that relieves excess pressure accidentally introduced via duct 36. Relieving excess pressure prevents that collapse of the thin walled section that may lead to complete obstruction of blood flow from the roller pump to the patient or the bursting of tubing 22 or damage to any other device in the arterial line.

Figure 4:
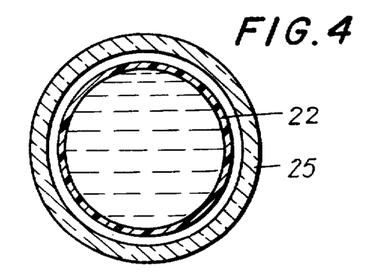
FIG. 4 is a transverse sectional view taken along the line 4—4 of FIG. 3, showing particularly the expanded configuration of the tubing member within the housing prior to contraction.

FIG. 4 shows housing 25 and tubing member 22 therein in a state where tubing member 22 expanded within housing 25. By expanded it is meant that the tubing assumes its normal enlarged dimension with negligible stress in the walls thereof. By providing slight clearance between the outside diameter of the enlarged section of the plastic tubing and the inside diameter of cavity 25a, it is insured that no air or other fluid can be trapped between the housing and the inner tubing which would prevent total expansion of the tubing and proper filling thereof. By the same token, it can be observed that upon introduction of pressure fluid through duct 36 into the cavity 25a such fluid is free to flow throughout the entire longitudinal extent of the housing 25 thereby applying pressure uniformly to the tubing along its entire length.

Figure 5:
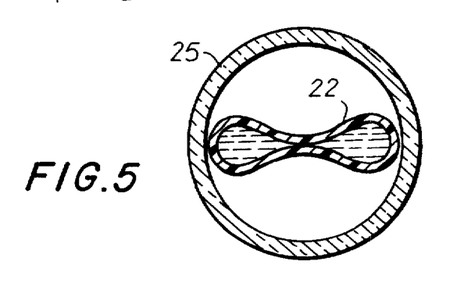
FIG. 5 is a transverse sectional view of the pulsator of FIG. 3 similar to that of FIG. 4 but with the tubing member shown contracted by means of fluid under pressure conducted to the housing by means of the driving unit of FIG. 1.

FIG. 5 shows tubing member 22 within housing 25 in a contracted condition which forces a pulse of blood from pulsator 24. It should be noted that the condition illustrated in FIG. 5 is less thans favorable in that opposing walls of the tubing 22 have been permitted to come into direct contact. Preferably, such direct contact should be avoided.

The pulses imparted to the blood by the pulsator may be intermittent depending on when fluid under pressure is conducted by conduit 30 to pulsator 24 and withdrawn therefrom as determined by driving unit 26 (FIG. 1). The intermittent pulses may be provided separately in a predetermined manner as during ventricular fibrillation, or they may be provided as counterpulsation between natural pulses of heart 12.

Figure 2:
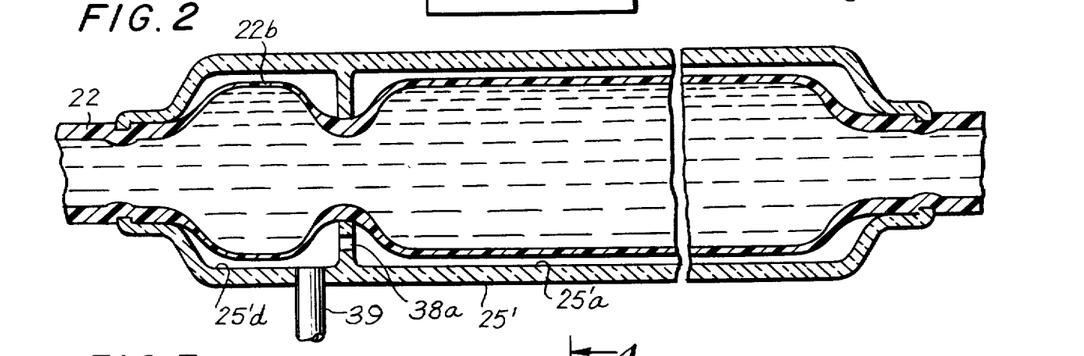
FIG. 2 is a sectional view taken along the line 2—2 of FIG. 1 and showing particularly a double cavity configuration of an alternative embodiment wherein a valve cavity is associated with a pulsator at the inlet end thereof.

Referring now to FIG. 2, another embodiment of the present invention is shown including a rigid housing 25' defining therewithin a housing cavity 25'a and a valve cavity 25'd. Such cavities may be separated by a baffle which includes an opening 38a for conducting fluid under pressure from the valve cavity 25'd to the housing cavity 25'a. Inlet 39 is provided for interconnecting conduit 30 directly with valve cavity 25'd wherein tubing member 22 is thinner walled at 22b relative to thin walled section 22a of FIG. 3, and quickly responds to the introduction of fluid under pressure for quick reaction with respect to contractions thereof. Subsequently, tubing member 22 within housing cavity 25'a 1 is contracted, *the delay occurring primarily because of the thicker walls within housing cavity 25'a with respect to* the portion of tubing member 22 within cavity 25'd. The size of orifice 38a may further control the delay although for rapid expansion of the tubing and rapid fluid intake the orifice 38a should be large enough to minimize throttling. Thus, the section of tubing within valve cavity 25'd will slow down flow significantly into the section of tubing within the housing cavity 25'a so that contractions of the tubing within the housing cavity 25'a will pulse efficiently a flow of blood outwardly and back-flow will be minimized.

It may prove more economical to produce tubing member 22 in the embodiment of FIG. 2 with walls of the same thickness, albeit thinner than the normal tube wall, both in cavity 25'a and cavity 25'd. In such case, orifice 38a should be fitted with suitable bi-directional valving such that the flow of fluid from cavity 25'd into cavity 25'a is appropriately throttled while flow in the reverse direction is substantially unimpeded. Preferably, a combination valve such as the umbrella/duckbill valve combinations manufactured by Vernay Laboratories, Inc. of Yellow Springs, Ohio, should be used.

A further modification of the embodiment of FIG. 2 contemplates replacing the orifice 38a by a separate inlet directly to cavity 25'a so that the timing of contractions can be assured by means of the sequence of introduction of fluid under pressure first to the valve cavity 25'd and then to the housing cavity 25'a.

Still another modification may include a branched conduit 30 wherein the same fluid control is coupled directly to both the valve cavity and the housing cavity with the thinner walls of the tubing within the valve cavity determining the the desired timing of the contractions (first in the valve cavity and then in the housing cavity).

Also, a valve cavity similar to valve cavity 25'd may be placed at the outlet end of housing 25' to thereby provide a device that will pump blood without a roller pump 20. Similar variations in conducting control fluid to the outlet valve cavity are available as were described with reference to the inlet valve cavity.

Accordingly, with the last-mentioned configuration and no oxygenator, one continuous unitary length of tubing from patient to patient and an overlying pulsator housing accomplishes all needed functions. If a reservoir or pressure-sensitive section of tubing 22 is required it may be provided in the system by simply expanding certain sections of the tubing, and providing appropriate housing where necessary. Also, at inlet and outlet portions of the tubing, cannulae may be formed directly on the two ends of tube 22 or added mechanically.

Whereas the embodiment of the pulsator illustrated in FIGS. 3, 4 and 5 is quite satisfactory, it is possible to improve the response thereof by eliminating some of the excess space between the interior of the housing and the exterior of the tubing. In particular, referring to FIG. 3, it will be seen that there is substantial space overlying the transition zones of the tubing within the ends of the housing 25. With this in mind, reference should be had to FIGS. 6 to 10 which illustrate a modification of the device capable of providing faster response and more reliable over pressure control. As seen therein, the flexible tubing 40, similar to tubing 22, has a region 41 intermediate its ends which region has an inside diameter greater than the inside diameter of the remainder of said tubing 40, and a thinner wall than that of the remainder of the tubing, with a gradual transition in wall thickness and diameter therebetween. A rigid walled enclosure 42 is provided surrounding the region 41 of said tubing with a slight clearance therebetween except at the ends of said enclosure which encircle said tubing beyond the region 41 with a snug fit which by appropriate control can provide an excess pressure relief mechanism as described previously. In addition, it will be observed that the interior of the end walls of the enclosure 42 are contoured to conform to the exterior surface of the transition section of tubing 40.

Figures 7, 8, 9, 10, 12:
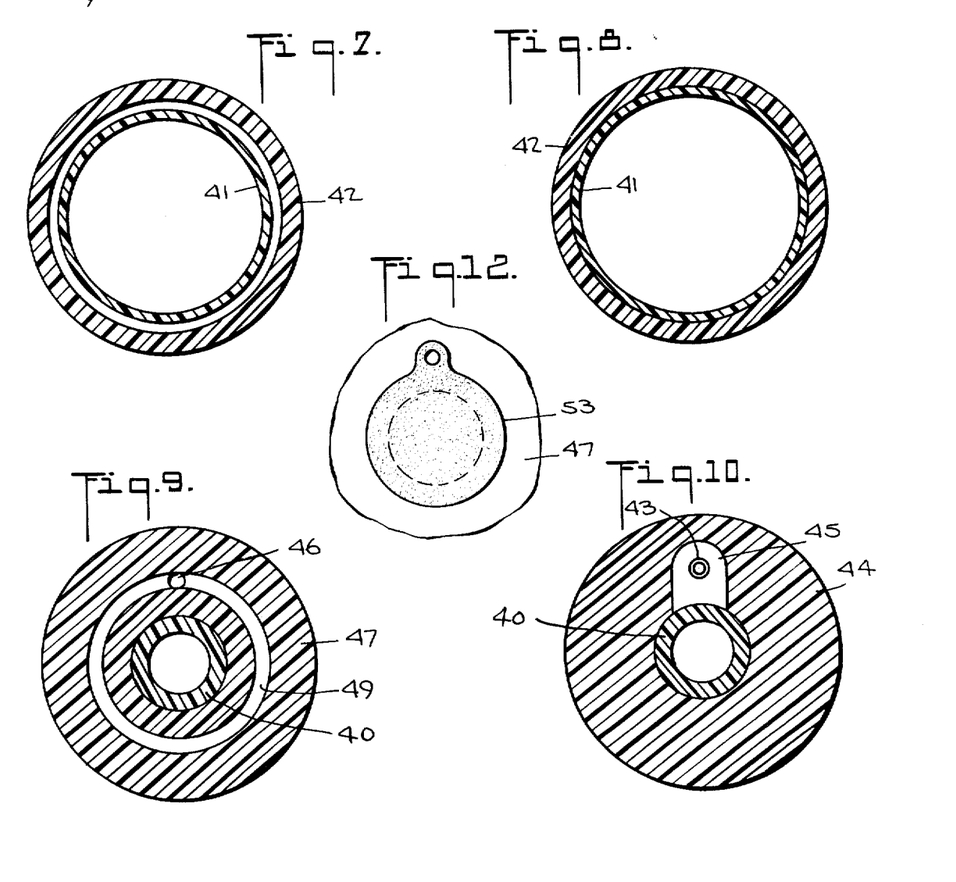
FIG. 7 is a transverse sectional view taken along the line 7—7 of FIG. 6.
FIG. 8 is a view similar to FIG. 7 but showing the internal tubing expanded into engagement with the walls of the surrounding enclosure.
FIG. 9 is a transverse sectional view taken along the lines 9—9 in FIG. 6 showing a venting port for the enclosure.
FIG. 10 is a transverse sectional view taken along the line 10—10 in FIG. 6 showing a detail in the construction of the end wall of the enclosure.
FIG. 12 is a plan view of a modified check valve employed in the embodiment of FIG. 11.

A duct 43 is joined to the enclosure 42 at one end 44 for interconnecting the driving unit, controlling the supply and withdrawal of pressurizing fluid, with the space between said enclosure 42 and the tubing region 41 at said one end 44 of the housing 42. As best seen in FIG. 10, the end wall 44 of the housing has a cavity or depression 45 formed therein to provide a communicating channel for conducting fluid between duct 43 and the radially outermost point of the housing interior. It also communicates with the unexpanded area of the tubing adjacent the end of enclosure 42 providing direct access to the "snug fit" overpressure relief mechanism.

Figure 6:
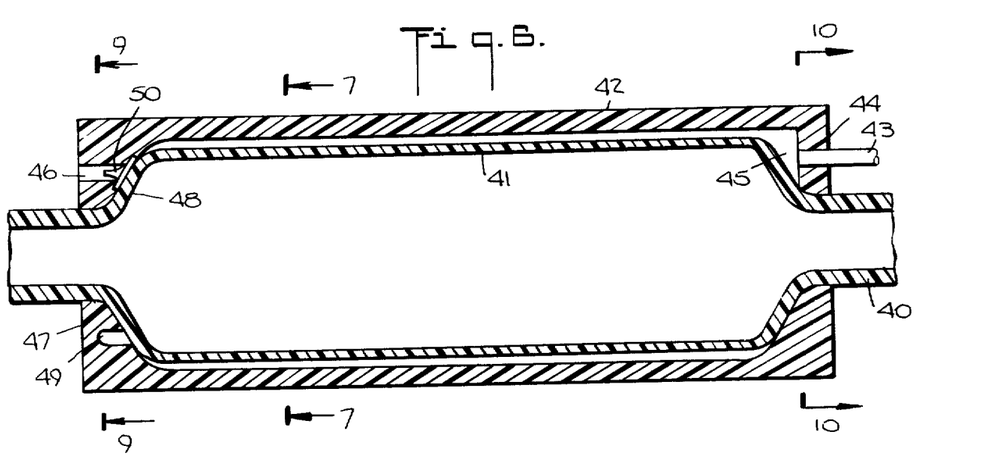
FIG. 6 is a longitudinal sectional view similar to FIG. 3 but showing a modification of the device.

In order to prevent pinching of the tubing region 41 by the pressure differential resulting from introduction of fluid through duct 43, various means may be provided. As an example, and as shown in FIGS. 6 and 9, there is provided a port 46 in the end wall 47 of housing 42 which port is normally occluded by the transition portion of tubing 40 when said tubing region 41 is free from indentations. Flexure characteristics of the tubing region 41 is such that the transition region 48 is displaced to uncover the port 46 only after tubing region 41 is indented to a predetermined limit. The extent to which port 46 is opened may be controlled by the degree of indentation of region 48 which, in turn, is a function of the variation in wall thickness. Such control can be arranged to provide for gradual interruption of blood flow thereby preventing high negative pressure surges and the attendant formation of microbubbles in the blood. As best seen in FIG. 9, the port 46 communicates with an annular groove 49 to ensure adequate venting. If necessary, the port 46 may be provided with a check valve 50 preventing air from re-entering the enclosure 42 through port 46 when fluid is being withdrawn or evacuated from enclosure 42 via duct 43 for the purpose of expanding the tubing region 41. A duckbill valve or any other suitable valve known to the art may be employed for this purpose.

With appropriate dimensioning, it is possible to employ the pressure relief afforded by port 46 and its interrelationship with the tubing region 48 to prevent total collapse or indentation of the central portion of the tubing such that opposing surfaces never come into direct contact and, therefore, no injury is imparted to the blood cells. Moreover, such venting insures that the outflowing blood cannot be interrupted as abruptly as it can be when full driving pressure is permitted to squeeze the tubing walls together. In other words, means are provided to prevent the central portion of the tubing from becoming pinched during operation of the device. It should be understood that the just described embodiment incorporates two relief valves. The first valve, provided by the tailored snug fit between tubing 40 and the end 44 of enclosure 42, functions to relieve excess drive pressure when communication with vent port 46 is blocked such as when the central portion 41 of the tube is full and the outlet end of tubing 40 is clamped off. Otherwise, relief is provided by the second valve consisting of port 46, tube section 48 and element 50.

Comparing FIGS. 7 and 8, it should be understood that the tubing region 41 has a "neutral" condition with a normally unstressed diameter slightly smaller than the inside diameter of the housing 42, although blood pressure within the tubing or negative pressure from the driving unit may cause enlargement of the region 41 such that the tubing engages the walls of the housing 42. The dynamics of the apparatus are such that the tubing will assume its "neutral" condition as shown in FIG. 7 throughout its length before any portion of said tubing contacts the wall of the housing 42. Since the clearance between the housing and the tubing is normally slight, only negligible air or other fluid can be trapped between the surfaces.

Figure 11:
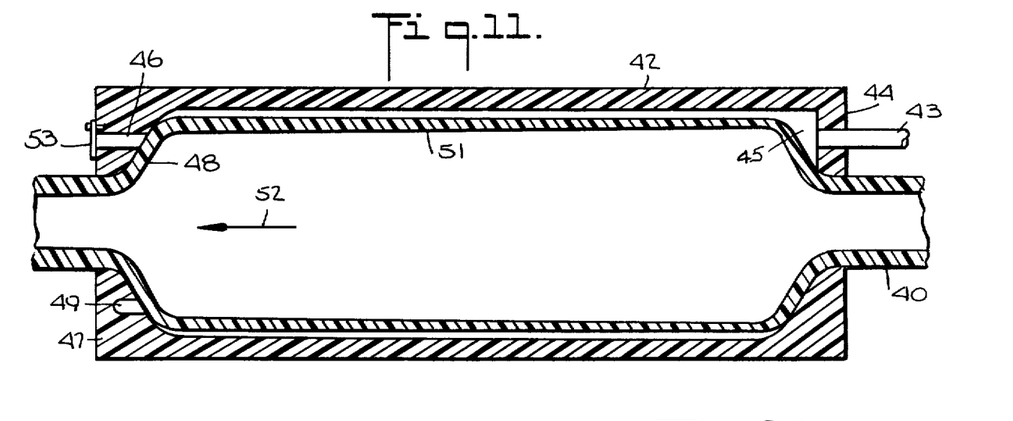
FIG. 11 is a longitudinal sectional view similar to FIG. 6 but showing a modification thereof wherein the wall of the central section of the tubular member is graduated in thickness from one end of the device to the other.

With only slight modification to the structure shown in FIG. 6, it is possible to provide for imparting directional flow to the blood contained therein. As shown in FIG. 11 the tubing region 51 has the thickness of its wall graduated axially with the thinner zone being adjacent the one end 44 of the housing 42 which contains the inlet duct 43. It will be understood that the varying wall thickness causes the indentation of the tubing region 51 to progress axially from the one end adjacent wall 44 to the other end for imparting directional flow to blood contained therein. That is, flow will be caused to occur in the direction of the arrow 52. In all other respects, the embodiment of FIG. 11 is similar to the embodiment shown in FIG. 6 except that internal check valve 50 has been replaced by an external flap valve 53, the details of which are shown in FIG. 12. While a flap valve will function as required it is susceptible of inadvertent interference since it is exposed and should be replaced with an internal valve 50 where the possibility of interference is deemed objectionable.

Instead of or supplementing the graduated wall thickness of tubing 51, said tubing region can be treated appropriately to impart thereto a controlled variation in resilience with the region adjacent enclosure end 44 being softer and more flexible than the region at the opposite end of the device.

Figures 13, 14, 15, 16, 17:
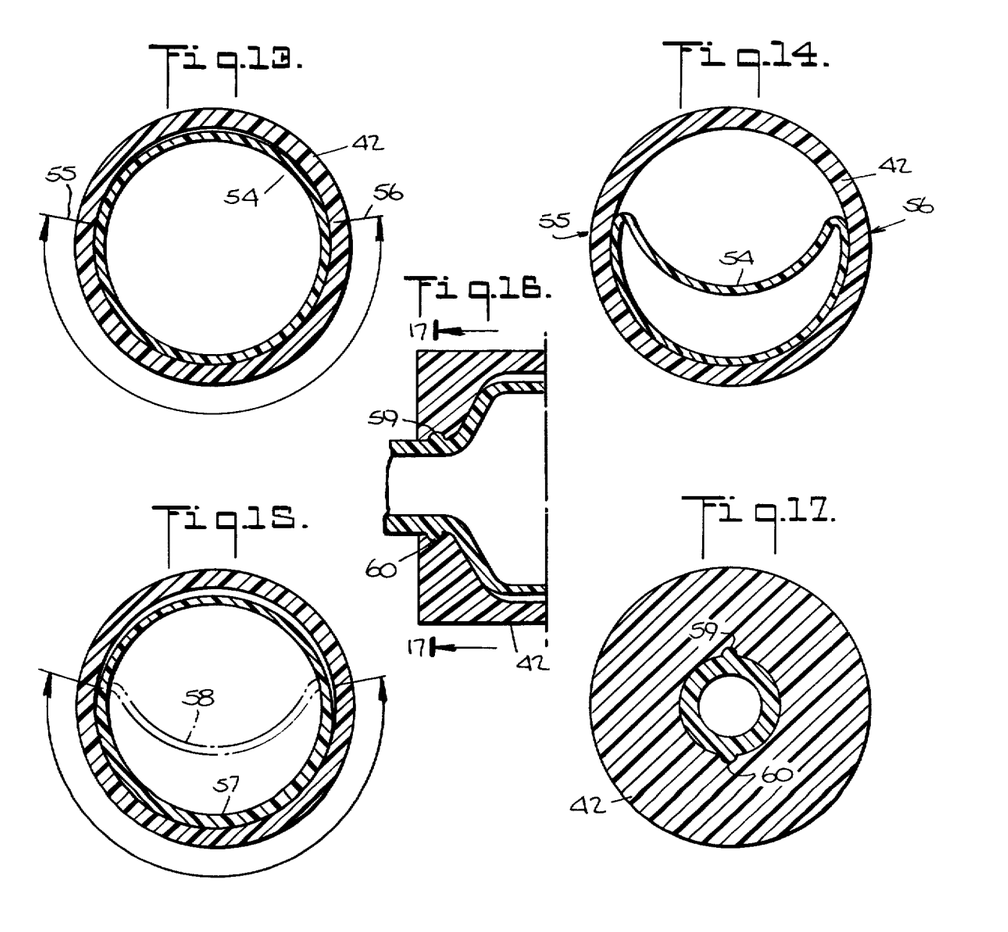
FIG. 13 is a view similar to FIG. 7 but showing a further modification of the device in order to restrict the indentation or collapse of the section of tubing within the enclosure.
FIG. 14 is a view similar to FIG. 13 but showing the tubing in its maximum indented condition.
FIG. 15 is a view similar to FIG. 13 but showing a modified arrangement for restricting the indentation of the tubing.
FIG. 16 is a fragmentary longitudinal sectional view of one end of the enclosure and tubing showing an arrangement for keying the tubing to the enclosure.
FIG. 17 is a transverse sectional view taken along line 17—17 in FIG. 16.

Alternative means for limiting the indentation of the contractible region of the tubing will now be described by first referring to FIGS. 13 and 14 wherein the tubing 54 is bonded over a little more than half of its circumference between the longitudinal elements 55 and 56 to the inner surface of the housing 42. The unbonded circumference of tubing 54 may still remain spaced from the inner surface of housing 42 as illustrated in FIG. 13. When fluid is introduced via duct 43 to the housing 42 it will cause indentation of the tubing section 54 to the limiting extent shown in FIG. 14.

Instead of cementing or otherwise bonding the tubing wall to the enclosure wall, it is possible to thicken the wall of the tubing over the same region as shown at 57 in FIG. 15 relying upon the additional resistance and strength of the tubing wall to prevent indentation beyond that shown by the dotted lines 58.

Depending upon the nature of the construction of the device, it may be desirable to provide means for preventing relative rotation between the enclosure 42 and the tubing 22 or 40 passing therethrough. This may be accomplished conveniently as shown in FIGS. 16 and 17 by providing ears 59 and 60 on the tubing extending into respective recesses in the end wall of the housing. At the same time said interrelationship between the ears 59, 60 and the housing will prevent axial movement between the tubing and the housing. Alternatively, localized or spot cementing may be employed instead of the ears 59 and 60.

Figure 18:
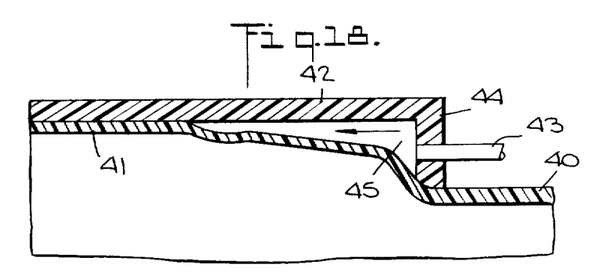
FIG. 18 is a fragmentary view of the upper righthand quadrant of a modified embodiment of the device similar to FIG. 6 but showing the effect of controlled adhesion.
Figure 19:
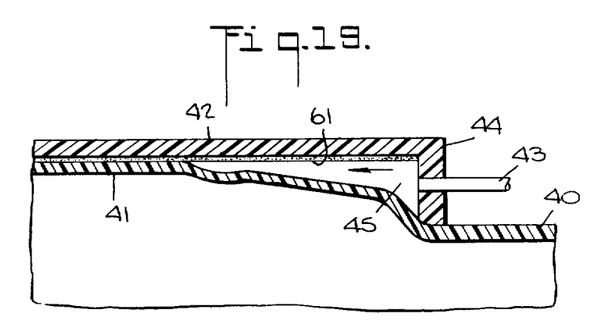
FIG. 19, is a view similar to FIG. 18, but showing the use of a coating layer for controlled adhesion.

Referring again to FIG. 8, with slight internal blood pressure or evacuation of the enclosure 42 the region 41 of the tubing may be caused to engage the inner wall of the encircling housing. If the internal pressure is sufficient it should be recognized that as fluid pressure is introduced through duct 43 and recess 45 to the interior of housing 42 the tubing must be contracted gradually in the axial direction in order to permit access of the pressure fluid longitudinally through the housing from the inlet end to the opposite end containing the relief port 46. Additional control of this progressive contraction may be effected as shown in FIG. 19 by introducing a layer 61 of silicone grease or similar material between the housing 42 and the tubing 41 to develop controlled adhesion therebetween. Alternatively, as seen in FIG. 18, if the housing and tubing are both fabricated from suitable grades of polyvinyl chloride the materials will have a naturally adherent characteristic. In each instance, the progressive contraction will impart directional flow to the blood carried therethrough.

Figure 20:
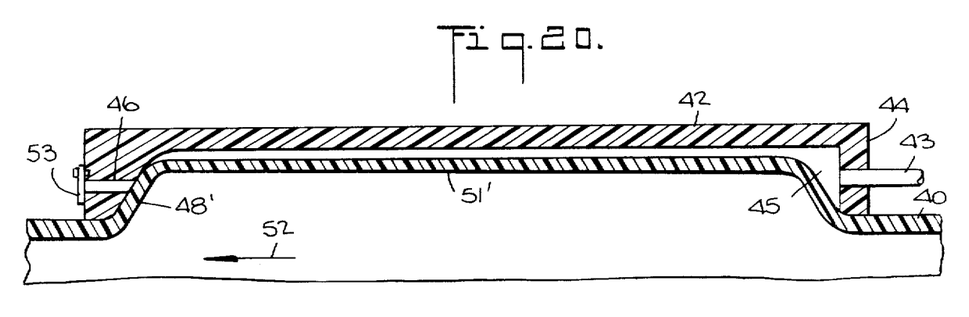
FIG. 20 is a fragmentary longitudinal view similar to FIG. 11 but showing a modification thereof.

Referring to FIG. 11, and using controlled adhesion to impart directional blood flow, minimization of trapped air or other fluid between tubing 51 and the enclosure 42 can be achieved by reversing the direction in which the wall thickness of tubing 51 tapers such that the thicker portion is at the end 44 of enclosure 42 and the thinner portion is at the opposite end of the device. This is illustrated in FIG. 20. With such construction, i.e., the reversal of the taper, during a filling cycle of tubing section 51', it will, as discussed previously, expand to the neutral condition shown in FIG. 20. Further expansion will occur first in the thin walled region which is now located remote from duct 43 to engage the wall of enclosure 42. Thereafter the expansion of the wall of tubing region 51' will progress longitudinally toward the end wall 44 and duct 43. This permits complete evacuation of the enclosure 42. On the pressure cycle with the introduction of fluid through duct 43 the abovementioned controlled adhesion will cause the tubing region 51' nearest the duct 43 to contract first with the progression moving longitudinally towards the opposite end of the device and thereby ejecting the blood with directional control. This arrangement minimizes the possibility of entrapping fluid within the housing 42 and maximizes the blood volume that can be pumped for any given size device.

Having described the presently preferred embodiments of the invention with reference to the accompanying drawings, it will be understood that various changes in detail may be imparted thereto without departing from the true spirit of the invention as defined in the appended claims. It should also be understood that since the main body of the tubing 22 and 40 has undiminished wall thickness and since it is not sealed to the pulsator housing at the housing ends, both the tubing strength and the venting arrangement at the ends of the pulsator housing cooperate to prevent the velocity sensitive fluttering encountered with prior devices.

What is claimed is:

1. A blood pulsating and/or pumping device for use in procedures involving transporting blood between two cannulae inserted in the body comprising a one-piece continuous length of blood compatible flexible polymeric tubing having a smooth inner surface which minimizes blood trauma throughout and including a normal first inside diameter, and a region intermediate the ends of said tubing formed by permanent expansion to have an expanded second inside diameter greater than said normal first inside diameter of the remainder of said tubing and a thinner wall than that of the remainder of said tubing with a gradual transition in wall thickness and diameter therebetween, a walled enclosure more rigid than said tubing region surrounding said region of said tubing with a clearance therebetween except at the ends of said enclosure which encircle said tubing beyond said region with a snug fit, and duct means joined to said enclosure for interconnecting the space between said enclosure and said tubing region with a driving unit for controlling the supply thereto and withdrawal therefrom of pressurizing fluid.

2. A device according to claim 1, wherein means are provided for preventing pinching of said tubing region by the pressure differential resulting from the supply of pressurizing fluid through said duct means into said enclosure.

3. A device according to claim 2, wherein said means for preventing pinching of said tubing region comprises means cooperatively related to said tubing for venting said space defined between said enclosure and said tubing whenever the indentation of said tubing exceeds a given limit.

4. A device according to claim 3, wherein said means for venting comprises a port through an end wall of said enclosure which port is normally occluded by a portion of said tubing when said tubing region is free from indentations, and the flexure characteristics of said tubing region is such that said portion of said tubing is displaced to uncover said port only after said tubing region is indented to said given limit.

5. A device according to claim 4, wherein said port is provided with a separate check valve.

6. A device according to claim 2, wherein said means for preventing pinching of said tubing region comprise means for limiting the indentation of said tubing region to a longitudinal zone having a circumferential arc length of less than 180°.

7. A device according to claim 6, wherein said means for limiting said indentation comprise a bond between said enclosure and the remainder of said tubing region outside of said longitudinal zone.

8. A device according to claim 6, wherein said means for limiting said indentation comprise a thicker tubing wall throughout the remainder of said tubing region outside of said longitudinal zone such that only the thinner walled longitudinal zone is free to indent under the force of said pressurizing fluid.

9. A device according to claim 1, wherein the thickness of the wall in said tubing region is graduated axially with the thinner area being adjacent one end of said enclosure such that indentation of said tubing region progresses axially from said one to the other end for imparting directional flow to blood contained therein.

10. A device according to claim 1, wherein said duct means is located near one end of said enclosure and said tubing region is adapted to expand into contact with the interior of said enclosure responsive to the withdrawal of pressurizing fluid from said enclosure, and means are provided for developing controlled adhesion between said enclosure and said tubing region whereby fluid introduced through said duct means can progressively peel said tubing from said enclosure in an axial direction to cause indentation of said tubing region to progress axially from said one end to the other end of said enclosure for imparting directional flow to blood contained therein.

11. A device according to claim 10, wherein said controlled adhesion is provided by a coating layer of silicone grease.

12. A device according to claim 10, wherein said controlled adhesion is provided by forming both said tubing and said enclosure from a grade of polyvinyl chloride that manifests adhesion when brought into contact.

13. A device according to claim 3, wherein said means for venting comprises a wall thickness in said tubing such that excessive fluid pressure in the space within said enclosure can cause indentation of said tubing where it passes through said ends of the enclosure to permit venting of said fluid between said tubing and said enclosure before indentation within said tubing region exceeds said given limit.

14. A device according to claim 1, wherein means are provided for keying said tubing relative to said enclosure to prevent relative rotation about their common longitudinal axis.

15. A device according to claim 6, wherein means are provided for keying said tubing relative to said enclosure to prevent relative rotation about their common longitudinal axis.

16. A device according to claim 8, wherein means are provided for keying said tubing relative to said enclosure to prevent relative rotation about their common longitudinal axis.

17. A device according to claim 1, wherein said duct means is located near one end of said enclosure and the thickness of the wall in said tubing region is graduated axially with the thicker area being adjacent one end of said enclosure such that expansion of said tubing region to eliminate said clearance responsive to withdrawal of said pressurizing fluid progresses axially from said other end to said one end so as to avoid entrapment of said pressurizing fluid in said space and ensure uniform engagement of said tubing region throughout its length with the wall of said enclosure.

18. A device according to claim 10, wherein the thickness of the wall in said tubing region is graduated axially with the thicker area being adjacent said one end of said enclosure such that said expansion of said tubing region into contact with the interior of said enclosure progresses axially from said other end to said one end so as to avoid entrapment of said pressurizing fluid in said space and ensure uniform engagement of said tubing region throughout its length with the wall of said enclosure.

19. The process for producing a blood pulsating and/or pumping device for use in procedures involving transporting blood between two cannulae inserted in the body which comprises the steps of selecting a continuous one-piece length of tubing of blood compatible flexible polymeric material having a smooth inner surface which minimizes blood trauma throughout, inelastically expanding at least one selected longitudinal section of said tubing intermediate the ends of said tubing so as to have an inside diameter throughout said section which is greater than the inside diameter of the remainder of said tubing and a thinner wall than said remainder of said tubing, with a gradual transition in wall thickness and diameter therebetween, surrounding said enlarged section of tubing with a walled enclosure more rigid than said section with clearance therebetween except at the ends of said enclosure which encircle said tubing beyond said enlarged section with a snug fit, and providing at least one duct means in said enclosure for interconnecting a driving unit thereto to control the supply and withdrawal of pressurizing fluid to the space between said enclosure and said section of said tubing.

* * * * *